(12) United States Patent
Wang et al.

(10) Patent No.: US 10,034,604 B2
(45) Date of Patent: Jul. 31, 2018

(54) OPTICAL MEASURING APPARATUS AND OPERATING METHOD THEREOF

(71) Applicant: Crystalvue Medical Corporation, Taoyuan (TW)

(72) Inventors: William Wang, Taoyuan (TW); Meng-Shin Yen, Taipei (TW); Chung-Cheng Chou, Luzhu Township (TW); Chung-Ping Chuang, Taoyuan (TW)

(73) Assignee: Crystalvue Medical Corporation, Taoyuan (TW)

( * ) Notice: Subject to any disclaimer, the term of this patent is extended or adjusted under 35 U.S.C. 154(b) by 2 days.

(21) Appl. No.: 15/487,119

(22) Filed: Apr. 13, 2017

(65) Prior Publication Data

US 2017/0303780 A1    Oct. 26, 2017

Related U.S. Application Data

(60) Provisional application No. 62/322,287, filed on Apr. 14, 2016.

(51) Int. Cl.
*A61B 3/10* (2006.01)
*A61B 3/00* (2006.01)

(52) U.S. Cl.
CPC .......... *A61B 3/0008* (2013.01); *A61B 3/1005* (2013.01)

(58) Field of Classification Search
CPC ............................ A61B 3/0008; A61B 3/1005
USPC ......................................... 351/200, 205, 221
See application file for complete search history.

(56) References Cited

U.S. PATENT DOCUMENTS 9,658,103 B2 *   5/2017   Bernhard ................. G01J 3/12
2017/0251918 A1 * 9/2017   Plaian ...................... A61B 3/12

FOREIGN PATENT DOCUMENTS

CA            002830452 A1 *   4/2012   ......... A61F 9/00821

* cited by examiner

*Primary Examiner* — Tuyen Tra
(74) *Attorney, Agent, or Firm* — Patterson + Sheridan, LLP (57) ABSTRACT

An optical measuring apparatus includes a first light source, a second light source and a switching unit. The first light source is used to emit a first light toward a first direction. The second light source is used to emit a second light toward a second direction. The switching unit selectively switches to a first mode or a second mode. When the switching unit switches to the first mode, it blocks the second light and let the first light emitted to an aiming region on eyeball to perform an optical aiming and determine an eye axis center position on the eyeball; when the switching unit switches to the second mode, the switching unit changes the second light from the second direction to the first direction to let the second light emitted to the eye axis center position on the eyeball to perform an optical measurement.

20 Claims, 6 Drawing Sheets

OPTICAL MEASURING APPARATUS AND OPERATING METHOD THEREOF

BACKGROUND OF THE INVENTION

1. Field of the Invention

This invention relates to optical detection, especially to an optical measuring apparatus and operating method thereof.

2. Description of the Prior Art

In general, the conventional eye axis length measuring apparatus is a contact-type ultrasonic scanner. However, because the contact-type ultrasonic scanner will contact and press on the eyeball, it is possible that measurement error is generated due to inadvertent operation or wrong position is measured because the patient is tense. Therefore, if non-contact optical eye axis length measuring apparatus is used, the above-mentioned problems can be solved.

Figure 1A:
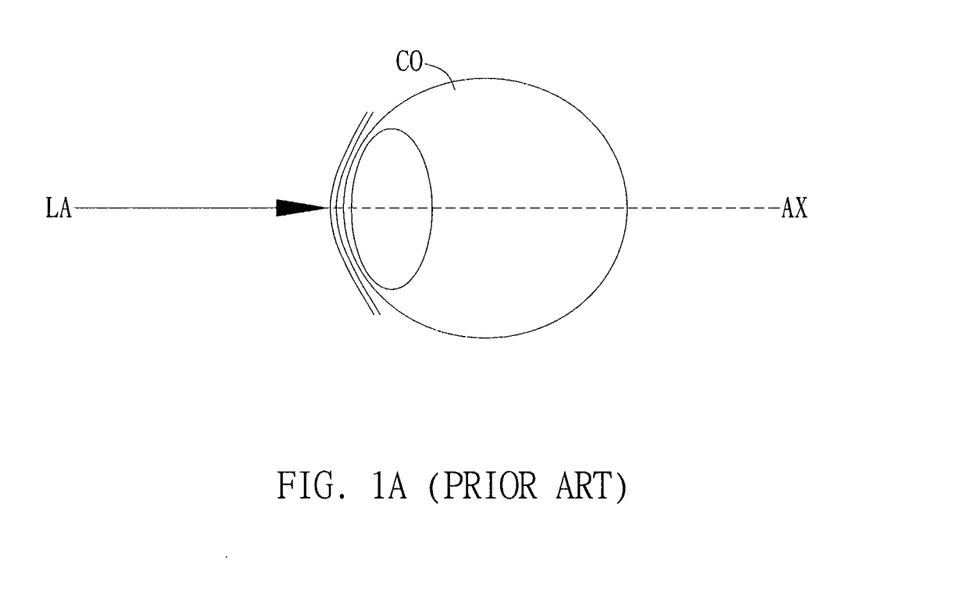
FIG. 1A and FIG. 1B illustrate schematic diagrams of the ideal state and deviated state of the optical measuring apparatus performing optical aiming process in the prior art respectively.

In the, actual operation of the optical measuring apparatus, it usually includes: (1) optical aiming process and (2) optical measurement process. As shown in FIG. 1A, the optical measuring apparatus can perform the optical aiming process (e.g., emitting to an aiming light LA to the eyeball CO and receiving its reflecting light) to enhance the measurement accuracy of the optical measuring apparatus.

Figure 1B:
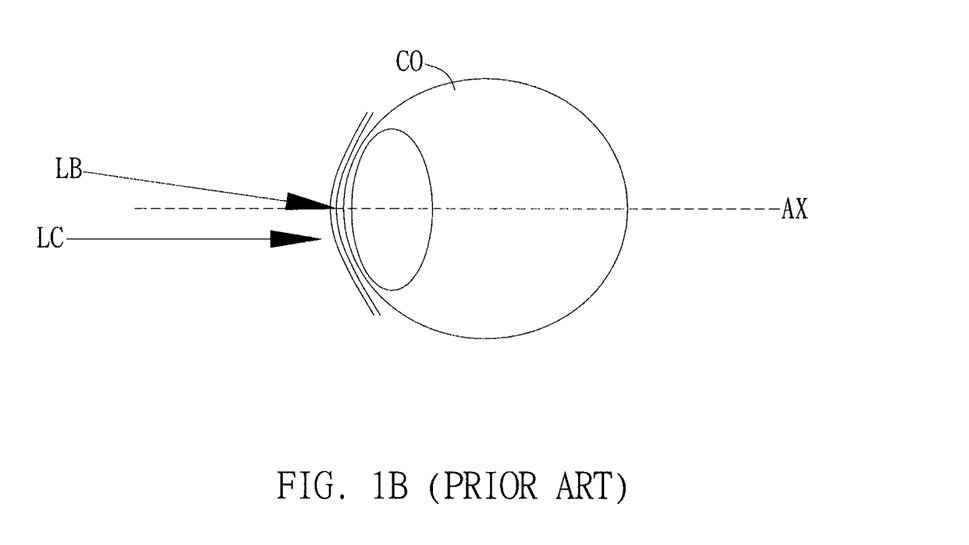

However, the actual operation is not the same as the ideal state shown in FIG. 1A. For example, as shown in FIG. 1B, once the aiming lights LB and LC emitted by the optical measuring apparatus are deviated (e.g., deviation from the eye axis AX), it will lead to aiming failure of the optical measuring apparatus, and the measurement accuracy of the optical measuring apparatus will be also seriously affected. As a result, the reliability of the measurement results will be significantly reduced and fail to be used as important reference for the evaluation of ophthalmology treatment.

SUMMARY OF THE INVENTION

Therefore, the invention provides an optical measuring apparatus and operating method thereof to overcome the problems occurred in the above-mentioned prior arts.

A preferred embodiment of the invention is an optical measuring apparatus. In this embodiment, the optical measuring apparatus includes a first light source, a second light source and a switching unit. The first light source is used to emit a first light toward a first direction. The second light source is used to emit a second light toward a second direction. The switching unit selectively switches to a first mode or a second mode. When the switching unit switches to the first mode, it blocks the second light and let the first light emitted to an aiming region on an eyeball to perform an optical aiming and determine an eye axis center position on the eyeball; when the switching unit switches to the second mode, the switching unit changes the second light from the second direction to the first direction to let the second light emitted to the eye axis center position on the eyeball to perform an optical measurement.

In an embodiment, the second direction is vertical to the first direction.

In an embodiment, when the switching unit switches to the first mode, the switching unit is parallel to the first direction, the switching unit is located in a path of the second light emitting toward the second direction to block the second light and the switching unit is located out of a path of the first light emitting toward the first direction.

In an embodiment, when the switching unit switches to the second mode, the switching unit is parallel to a direction between the first direction and the second direction, the switching unit is located in a path of the first light emitting toward the first direction to block the first light and the switching unit is located in a path of the second light emitting toward the second direction to change an emitting direction of the second light from the second direction to the first direction, so that the first light and the second light are emitted toward the eyeball alternately.

In an embodiment, when the switching unit switches to the second mode, the switching unit is parallel to a direction between the first direction and the second direction, the switching unit is located in a path of the first light emitting toward the first direction to let the first light pass the switching unit and continuously emitted toward the first direction; the switching unit is located in a path of the second light emitting toward the second direction to change an emitting direction of the second light from the second direction to the first direction, so that the first light and the second light are emitted toward the eyeball simultaneously.

Another embodiment of the invention is also an optical measuring apparatus. In this embodiment, the optical measuring apparatus includes a first light source, a second light source and a switching unit. The first light source is used to emit a first light toward a first direction. The second light source is disposed parallel to the first light source and configured to emit a second light toward the first direction. The switching unit is coupled to the first light source and the second light source and used for selectively switching to a first mode or a second mode. When the switching unit switches to the first mode, the switching unit moves the first light source to let the first light emitted to an aiming region on the eyeball to perform an optical aiming and determine an eye axis center position on the eyeball; when the switching unit switches to the second mode, the switching unit moves the second light source to let the second light emitted to the eye axis center position on the eyeball to perform an optical measurement.

Another embodiment of the invention is an optical measuring apparatus operating method. In this embodiment, the optical measuring apparatus operating method is used for operating an optical measuring apparatus to perform optical measurement. The optical measuring apparatus includes a first light source, a second light source and a switching unit. The first light source emits a first light toward a first direction and the second light source emits a second light toward a second direction. The switching unit selectively switches to a first mode or a second mode.

The optical measuring apparatus operating method includes steps of: when the switching unit switches to the first mode, the switching unit blocks the second light and let the first light emitted to an aiming region on an eyeball to perform an optical aiming and determine an eye axis center position on the eyeball; and when the switching unit switches to the second mode, the switching unit changes an emitting direction of the second light from the second direction to the first direction to let the second light emitted to the eye axis center position on the eyeball to perform an optical measurement.

Another embodiment of the invention is also an optical measuring apparatus operating method. In this embodiment, the optical measuring apparatus operating method is used for operating an optical measuring apparatus to perform optical measurement. The optical measuring apparatus includes a first light source, a second light source and a switching unit. The second light source is disposed parallel to the first light source. The first light source emits a first light toward a first direction and the second light source emits a second light toward the first direction. The switching unit selectively switches to a first mode or a second mode.

The optical measuring apparatus operating method includes steps of: when the switching unit switches to the first mode, the switching unit moves the first light source to let the first light emitted to an aiming region on an eyeball to perform an optical aiming and determine an eye axis center position on the eyeball; and when the switching unit switches to the second mode, the switching unit moves the second light source to let the second light emitted to the eye axis center position on the eyeball to perform an optical measurement.

Compared to the prior art, the optical measuring apparatus and operating method thereof in the invention can effectively improve the drawback that the optical measuring apparatus fails to aim in the prior art to enhance the measurement accuracy of the optical measuring apparatus. Therefore, the reliability of the measurement results can be significantly increased and used as important reference for the evaluation of ophthalmology treatment. In addition, the aiming light and the measuring light used in the optical measuring apparatus and operating method thereof in the invention can use different transmission channels (paths) respectively through moving the light sources or share the same transmission channel (path) through switching lights; the optical aiming process and the optical measuring process can be performed alternately or simultaneously, so that the flexibility of the optical measuring apparatus in practical applications can be also increased.

The advantage and spirit of the invention may be understood by the following detailed descriptions together with the appended drawings.

DETAILED DESCRIPTION OF THE INVENTION

A preferred embodiment of the invention is an optical measuring apparatus. In this embodiment, the optical measuring apparatus is used for measuring an eyeball to obtain an axis length of the eyeball, but not limited to this.

In general, the optical measuring apparatus usually includes a light source module, a plurality of optical components and an image analysis unit; in this embodiment, the light source module of the optical measuring apparatus at least includes a first light source LS1 for optical aiming and a second light source LS2 for optical measurement. Not only including the above-mentioned components, the optical measuring apparatus of the invention also includes a switching module capable of switching to different operation modes.

Figure 2A:
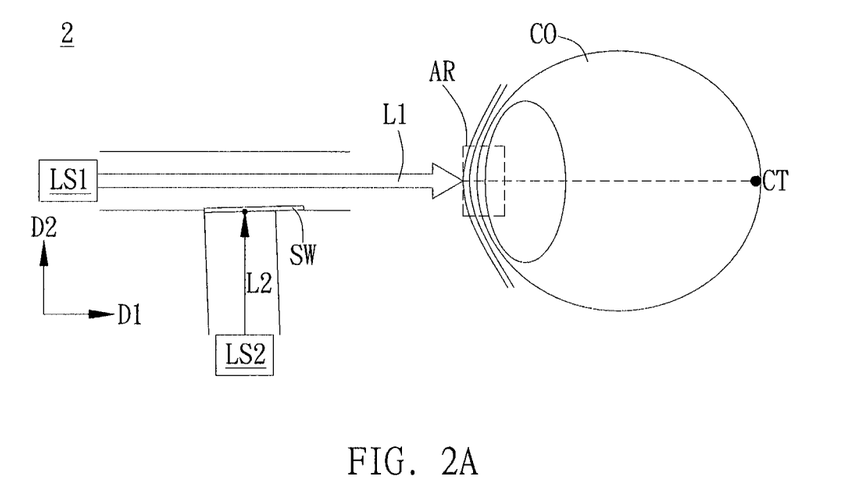
FIG. 2A and FIG. 2B illustrate schematic diagrams of the optical measuring apparatus in a preferred embodiment of the invention.
Figure 2B:
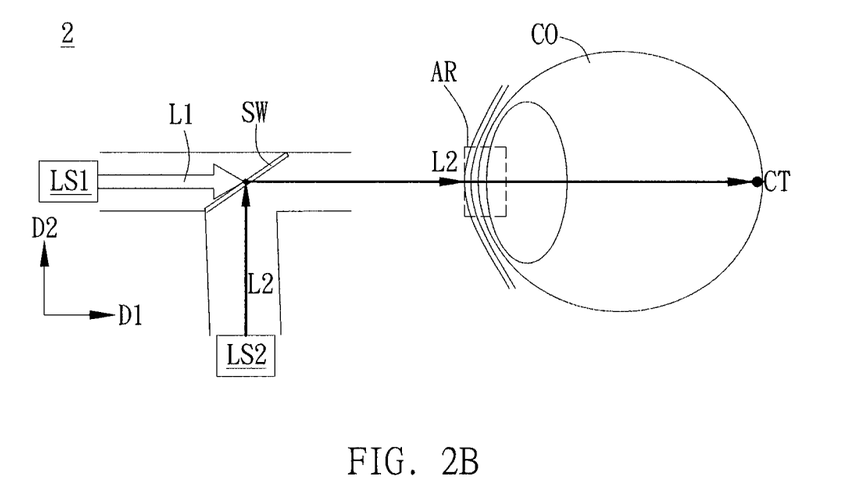

Please refer to FIG. 2A and FIG. 2B. FIG. 2A and FIG. 2B illustrate schematic diagrams of the optical measuring apparatus in a preferred embodiment of the invention. It should be noticed that, in this embodiment, the aiming light and the measuring light share the transmission channel (the transmission path) through a switching way, and the optical aiming process and the optical measuring process are performed alternately.

As shown in FIG. 2A, the optical measuring apparatus 2 includes a first light source LS1, a second light source LS2 and a switching unit SW. The first light source LS1 is used to emit a first light L1 toward a first direction D1. The second light source LS2 is used to emit a second light L2 toward a second direction D2. In this embodiment, the first light source LS1 is an aiming light source and the first light L1 is an aiming light; the second light source LS2 is a measuring light source and the second light L2 is a measuring light. The second direction D2 is vertical to the first direction D1. For example, the first direction D1 is the horizontal direction and the second direction D2 is the vertical direction, but not limited to this.

The switching unit SW can selectively switch to a first mode or a second mode. In this embodiment, the first mode can be called as optical aiming mode and the second mode can be called as optical measuring mode, but not limited to this.

When the switching unit SW switches to the first mode, the switching unit SW is arranged parallel to the first direction D1. Because the switching unit SW is located in a path of the second light L2 emitting toward the second direction D2 and located out of a path of the first light L1 emitting toward the first direction D1, the switching unit SW will block the second light L2 and let the first light L1 emitted to an aiming region AR on an eyeball CO to perform an optical aiming and determine an eye axis center position CT on the eyeball CO.

As shown in FIG. 2B, when the switching unit SW switches to the second mode, the switching unit SW will be parallel to a direction between the first direction D1 and the second direction D2, the switching unit SW is located in a path of the first light L1 emitting toward the first direction D1 to block the first light L1 and the switching unit SW is located in a path of the second light L2 emitting toward the second direction D2 to change an emitting direction of the second light L2 from the second direction D2 to the first direction D1, so that the first light L1 and the second light L2 can be emitted toward the eyeball CO alternately at different times.

Figure 3A:
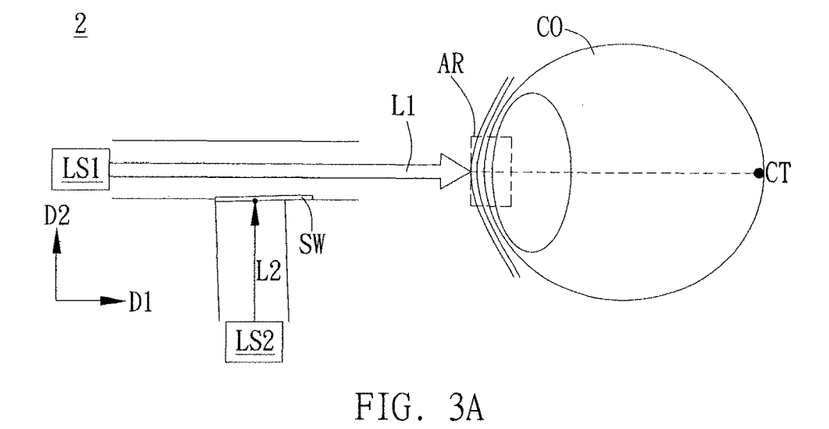
FIG. 3A and FIG. 3B illustrate schematic diagrams of the optical measuring apparatus in another preferred embodiment of the invention.
Figure 3B:
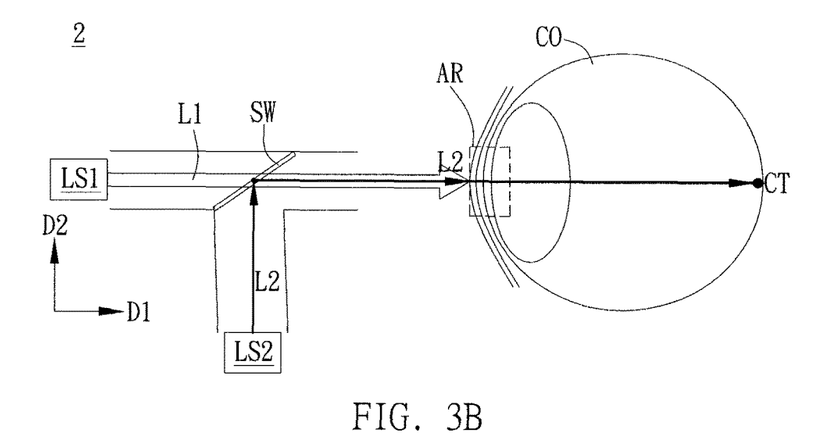

In another embodiment, please refer to FIG. 3A and FIG. 3B. FIG. 3A and FIG. 3B illustrate schematic diagrams of the optical eye axis length measuring apparatus in another preferred embodiment of the invention. It should be noticed that, in this embodiment, the aiming light and the measuring light share the transmission channel (the transmission path) through a switching way, and the optical aiming process and the optical measuring process are performed simultaneously.

The switching unit SW can selectively switch to a first mode or a second mode. In this embodiment, the first mode can be called as optical aiming mode and the second mode can be called as optical aiming and measuring mode, but not limited to this.

As shown in FIG. 3A, when the switching unit SW switches to the first mode, the switching unit SW is parallel to the first direction D1. Because the switching unit SW is located in a path of the second light L2 emitting toward the second direction D2 and located out of a path of the first light L1 emitting toward the first direction D1, the switching unit SW will block the second light L2 and let the first light L1 continuously emitted to the aiming region AR on the eyeball CO to perform an optical aiming and determine an eye axis center position CT on the eyeball CO.

As shown in FIG. 3B, when the switching unit SW switches to the second mode, the switching unit SW will be parallel to a direction between the first direction D1 and the second direction D2 (e.g., the angle between the direction and the horizontal direction and the angle between the direction and the vertical direction are both 45°, but not limited to this), so that the switching unit SW is located in a path of the first light L1 emitting toward the first direction D1 and in a path of the second light L2 emitting toward the second direction D2.

It should be noticed that the switching unit SW can be suitably designed to be passed by the first light L1 without blocking the first light L1, so that the first light L1 passing the switching unit SW can be continuously emitted to the eyeball CO along the first direction D1, and the switching unit SW also changes an emitting direction of the second light L2 from the second direction D2 to the first direction D1, so that the first light L1 and the second light L2 can be emitted toward the eyeball CO simultaneously. Since the first light L1 is an aiming light and the second light L2 is a measuring light, when the switching unit SW is switched to the second mode (e.g., the optical aiming and measuring mode), the optical measurement process can be performed with the optical aiming process at the same time.

Figure 3C:
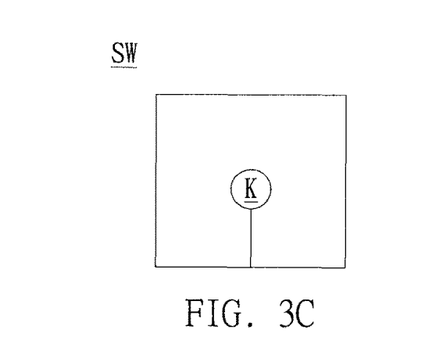
FIG. 3C illustrates a schematic diagram of the switching unit in FIG. 3A and FIG. 3B having a specific region.

In practical applications, in order to let the first light L1 pass the switching unit SW and let the second light L2 emitting along the second direction D2 originally be reflected to the first direction D1 by the switching unit SW, as shown in FIG. 3C, the switching unit SW can have a specific region K formed by certain optical material according to the first wavelength of the first light L1 and the second wavelength of the second light L2, so that when the first light L1 having the first wavelength is emitted to the specific region K of the switching unit SW, the first light L1 will pass through the specific region K and continuously emitted toward the first direction D1 and when the second light L2 having the second wavelength is emitted to the specific region K of the switching unit SW, the second light L2 will be reflected by the specific region K of the switching unit SW and emitted toward the first direction D1.

Another embodiment of the invention is also an optical measuring apparatus. Please refer to FIG. 4A~FIG. 4C, the optical measuring apparatus 4 includes a first light source LS1, a second light source LS2 and a switching unit SW. The switching unit SW selectively switches to a first mode or a second mode.

Figure 4A:
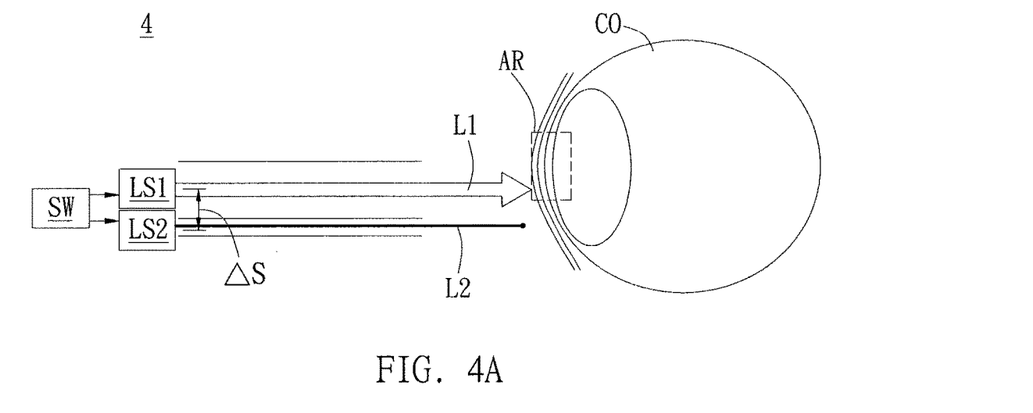
FIG. 4A, FIG. 4B and FIG. 4C illustrate schematic diagrams of the optical measuring apparatus in another preferred embodiment of the invention.
Figure 4B:
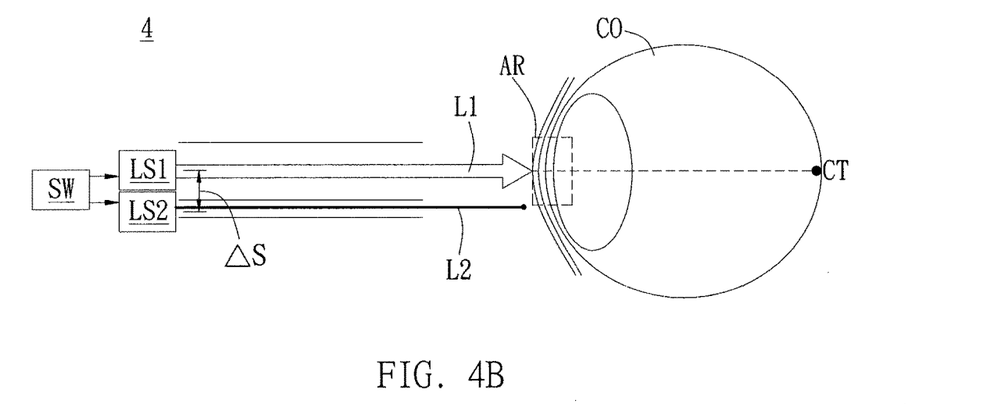
Figure 4C:
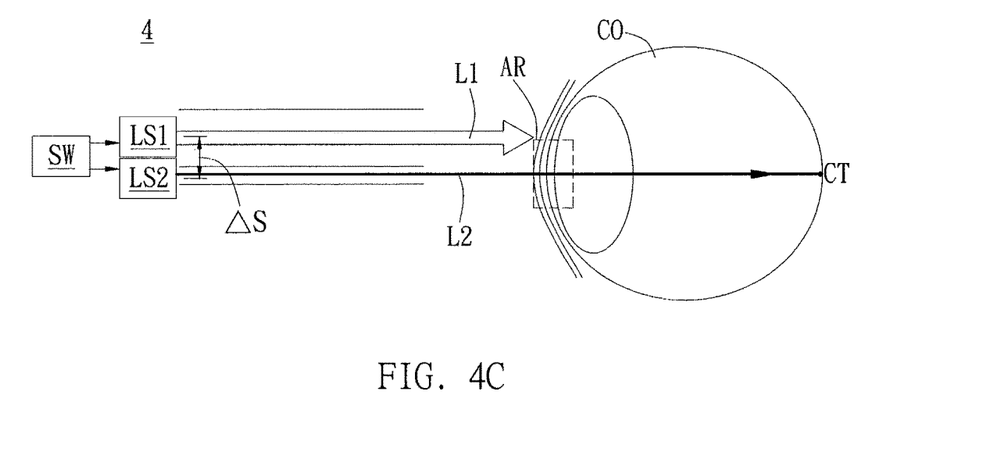

Different from the above-mentioned embodiment, the first light source LS1 and the second light source LS2 in this embodiment are arranged in parallel and there is a fixed distance ΔS between the first light source LS1 and the second light source LS2. The switching unit SW is coupled to the first light source LS1 and the second light source LS2. The first light source LS1 and the second light source LS2 emit the first light L1 and the second light L2 toward the first direction D1 (e.g., the horizontal direction) respectively.

As shown in FIG. 4A, when the switching unit SW switches to the first mode, the switching unit SW will move the first light source LS1 along the second direction (e.g., the vertical direction) to let the first light L1 from the first light source LS1 be emitted to an aiming region AR on the eyeball CO to perform an optical aiming and determine an eye axis center position CT on the eyeball CO as show in FIG. 4B.

As shown in FIG. 4C, when the switching unit SW switches to the second mode, the switching unit SW moves the second light source LS2 along the second direction (e.g., the vertical direction) to let the second light L2 from the second light source LS2 be emitted to the eye axis center position CT on the eyeball CO to perform an optical measurement. It should be noticed that the distance that the switching unit SW moves the second light source LS2 along the second direction D2 (e.g., the vertical direction) is the fixed distance ΔS between the first light source LS1 and the second light source LS2.

Another embodiment of the invention is an optical measuring apparatus operating method. In this embodiment, the optical measuring apparatus operating method is used for operating an optical measuring apparatus to perform optical measurement. The optical measuring apparatus includes a first light source, a second light source and a switching unit. The first light source emits a first light toward a first direction (e.g., the horizontal direction) and the second light source emits a second light toward a second direction (e.g., the vertical direction). The switching unit selectively switches to a first mode or a second mode.

Figure 5:
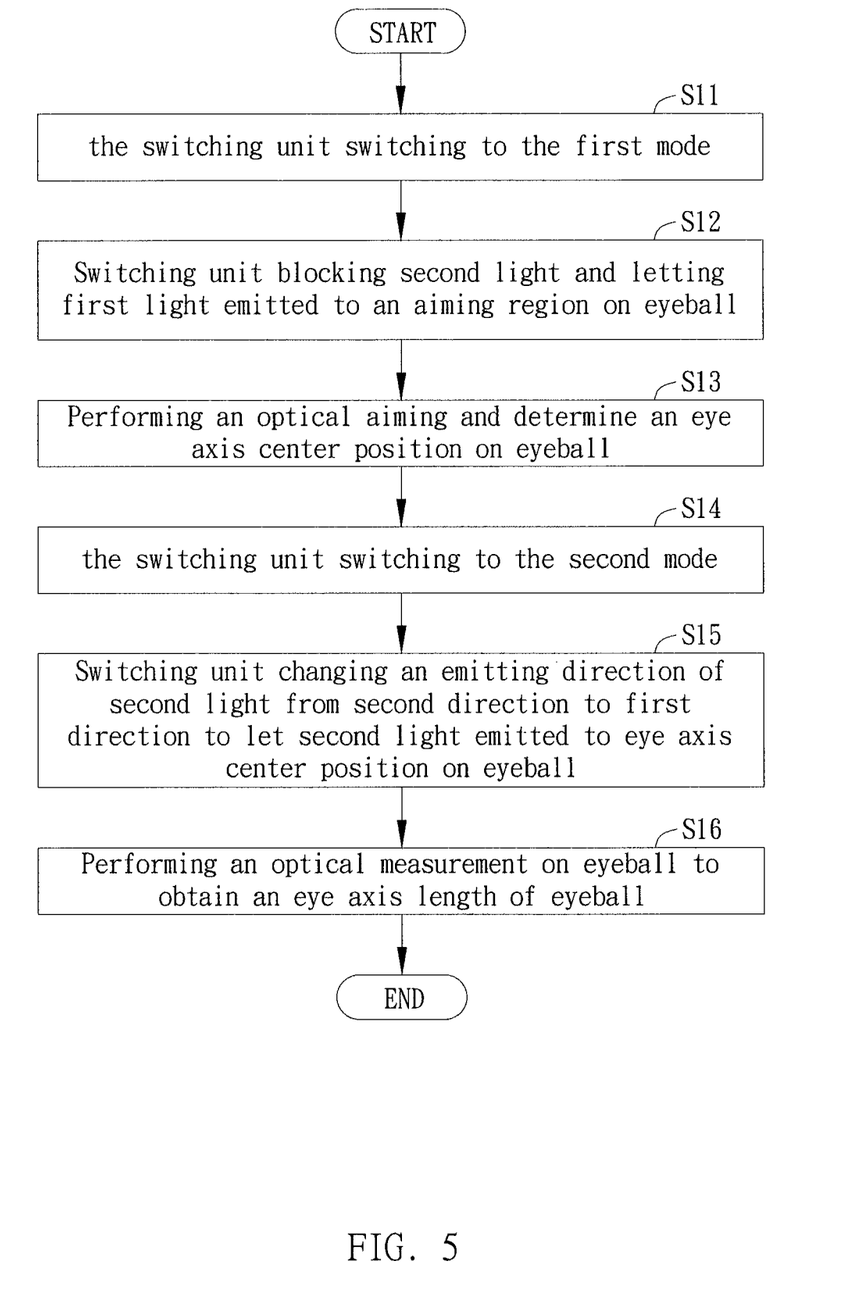
FIG. 5 illustrates a flowchart of the optical measuring apparatus operating method in another embodiment of the invention.

Please refer FIG. 5. FIG. 5 illustrates a flowchart of the optical measuring apparatus operating method in this embodiment. As shown in FIG. 5, the optical measuring apparatus operating method includes steps of:

Step S11: the switching unit switching to the first mode;

Step S12: the switching unit blocking the second light and letting the first light emitted to an aiming region on the eyeball;

Step S13: performing an optical aiming and determine an eye axis center position on the eyeball;

Step S14: the switching unit switching to the second mode;

Step S15: the switching unit changing an emitting direction of the second light from the second direction to the first direction to let the second light emitted to the eye axis center position on the eyeball; and Step S16: performing an optical measurement on the eyeball to obtain an eye axis length of the eyeball.

In practical applications, when the switching unit switches to the first mode (Step S11), the switching unit is parallel to the first direction, the switching unit is located in a path of the second light emitting toward the second direction to block the second light and the switching unit is located out of a path of the first light emitting toward the first direction to let the first light continuously emitted to an aiming region on the eyeball (Step S12).

When the switching unit switches to the second mode (Step S14), the switching unit is parallel to a direction between the first direction and the second direction, the switching unit is located in a path of the first light emitting toward the first direction and located in a path of the second light emitting toward the second direction at the same time.

In an embodiment, the switching unit will block the first light and change an emitting direction of the second light from the second direction to the first direction, so that the first light and the second light are emitted toward the eyeball alternately at different times.

In another embodiment, the switching unit will let the first light pass the switching unit and continuously emitted toward the first direction and change an emitting direction of the second light from the second direction to the first direction, so that the first light and the second light are emitted toward the eyeball simultaneously.

Another embodiment of the invention is also an optical measuring apparatus operating method. In this embodiment, the second light source is disposed parallel to the first light source and there is a fixed distance between them. The first light source emits a first light toward a first direction and the second light source emits a second light toward the first direction. The switching unit selectively switches to a first mode or a second mode.

Figure 6:
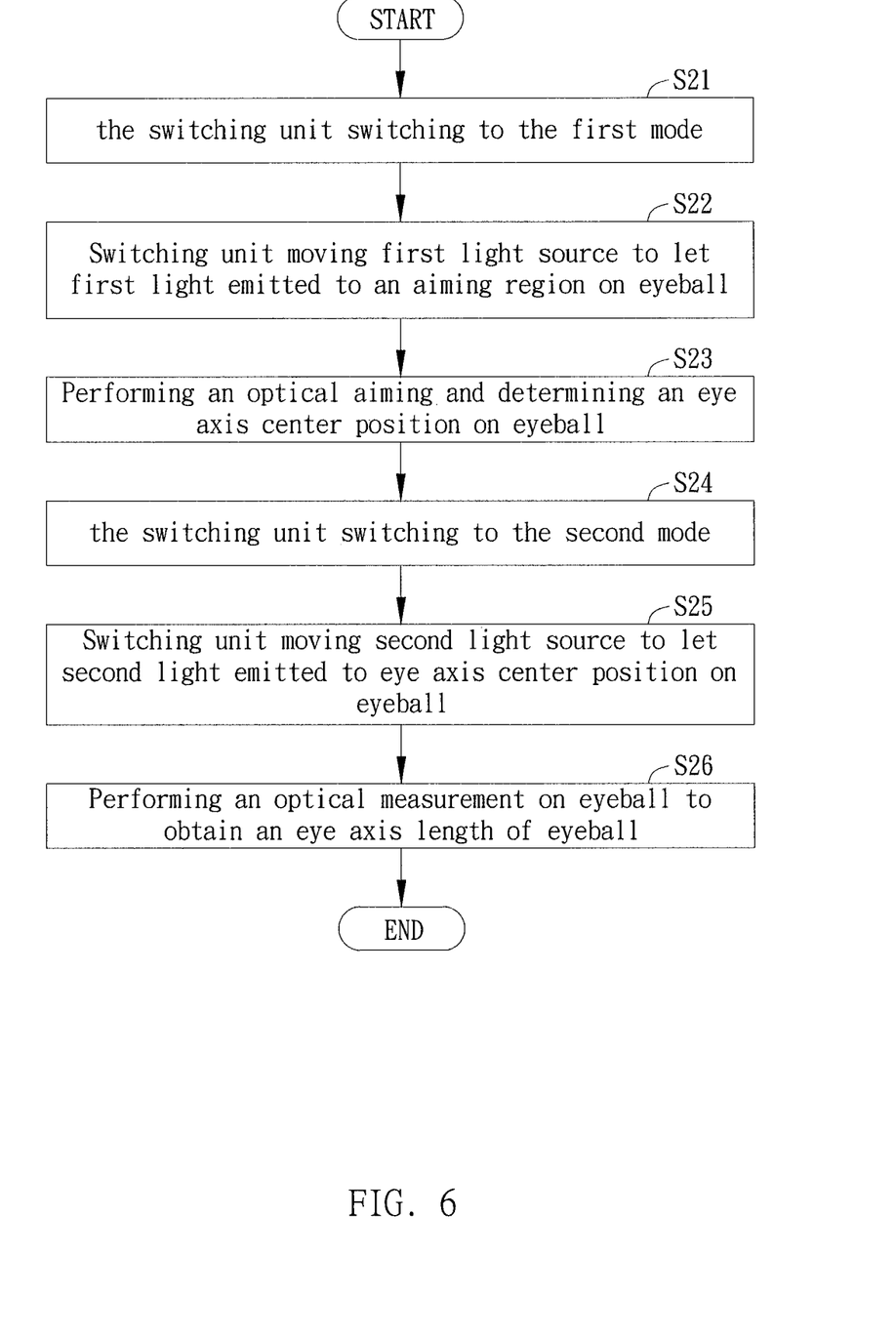
FIG. 6 illustrates a flowchart of the optical measuring apparatus operating method in another embodiment of the invention.

Please refer FIG. 6. FIG. 6 illustrates a flowchart of the optical measuring apparatus operating method in this embodiment. As shown in FIG. 6, the optical measuring apparatus operating method includes steps of:

Step S21: the switching unit switching to the first mode;

Step S22: the switching unit moving the first light source to let the first light emitted to an aiming region on the eyeball;

Step S23: performing an optical aiming and determining an eye axis center position on the eyeball;

Step S24: the switching unit switching to the second mode;

Step S25: the switching unit moving the second light source to let the second light emitted to the eye axis center position on the eyeball; and Step S26: performing an optical measurement on the eyeball to obtain an eye axis length of the eyeball.

In practical applications, the switching unit in Step S22 moves the first light source along a second direction (e.g., the vertical direction) and the switching unit in Step S25 moves the second light source along the second direction (e.g., the vertical direction), wherein the second direction is vertical to the first direction. It should be noticed that a distance that the switching unit moves the second light source along the second direction (e.g., the vertical direction) is the fixed distance between the first light source and the second light source.

Compared to the prior art, the optical measuring apparatus and operating method thereof in the invention can effectively improve the drawback that the optical measuring apparatus fails to aim in the prior art to enhance the measurement accuracy of the optical measuring apparatus. Therefore, the reliability of the measurement results can be significantly increased and used as important reference for the evaluation of ophthalmology treatment. In addition, the aiming light and the measuring light used in the optical measuring apparatus and operating method thereof in the invention can use different transmission channels (paths) respectively through moving the light sources or share the same transmission channel (path) through switching lights; the optical aiming process and the optical measuring process can be performed alternately or simultaneously, so that the flexibility of the optical measuring apparatus in practical applications can be also increased.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical measuring apparatus, comprising:
   a first light source configured to emit a first light toward a first direction;
   a second light source configured to emit a second light toward a second direction; and
   a switching unit selectively switching to a first mode or a second mode;
   wherein when the switching unit switches to the first mode, the switching unit blocks the second light and let the first light emitted to an aiming region on an eyeball to perform an optical aiming and determine an eye axis center position on the eyeball; when the switching unit switches to the second mode, the switching unit changes an emitting direction of the second light from the second direction to the first direction to let the second light emitted to the eye axis center position on the eyeball to perform an optical measurement.

2. The optical measuring apparatus of claim 1, wherein the second direction is vertical to the first direction.

3. The optical measuring apparatus of claim 1, wherein when the switching unit switches to the first mode, the switching unit is parallel to the first direction, the switching unit is located in a path of the second light emitting toward the second direction to block the second light and the switching unit is located out of a path of the first light emitting toward the first direction.

4. The optical measuring apparatus of claim 1, wherein when the switching unit switches to the second mode, the switching unit is parallel to a direction between the first direction and the second direction, the switching unit is located in a path of the first light emitting toward the first direction to block the first light and the switching unit is located in a path of the second light emitting toward the second direction to change an emitting direction of the second light from the second direction to the first direction, so that the first light and the second light are emitted toward the eyeball alternately.

5. The optical measuring apparatus of claim 1, wherein when the switching unit switches to the second mode, the switching unit is parallel to a direction between the first direction and the second direction, the switching unit is located in a path of the first light emitting toward the first direction to let the first light pass the switching unit and continuously emitted toward the first direction; the switching unit is located in a path of the second light emitting toward the second direction to change an emitting direction of the second light from the second direction to the first direction, so that the first light and the second light are emitted toward the eyeball simultaneously.

6. An optical measuring apparatus, comprising:
   a first light source configured to emit a first light toward a first direction;
   a second light source disposed parallel to the first light source and configured to emit a second light toward the first direction; and
   a switching unit, coupled to the first light source and the second light source, for selectively switching to a first mode or a second mode;
   wherein when the switching unit switches to the first mode, the switching unit moves the first light source to let the first light emitted to an aiming region on the eyeball to perform an optical aiming and determine an eye axis center position on an eyeball; when the switching unit switches to the second mode, the switching unit moves the second light source to let the second light emitted to the eye axis center position on the eyeball to perform an optical measurement.

7. The optical measuring apparatus of claim 6, wherein when the switching unit switches to the first mode, the switching unit moves the first light source along a second direction, and the second direction is vertical to the first direction.

8. The optical measuring apparatus of claim 6, wherein when the switching unit switches to the second mode, the switching unit moves the second light source along a second direction, and the second direction is vertical to the first direction.

9. The optical measuring apparatus of claim 6, wherein there is a fixed distance between the first light source and the second light source which are disposed in parallel.

10. The optical measuring apparatus of claim 9, wherein when the switching unit switches to the second mode, a distance that the switching unit moves the second light source is the fixed distance.

11. An optical measuring apparatus operating method for operating an optical measuring apparatus to perform optical measurement, the optical measuring apparatus comprising a first light source, a second light source and a switching unit, the first light source emitting a first light toward a first direction and the second light source emitting a second light toward a second direction, the switching unit selectively switching to a first mode or a second mode, the optical measuring apparatus operating method comprising steps of:
when the switching unit switches to the first mode, the switching unit blocking the second light and letting the first light emitted to an aiming region on an eyeball to perform an optical aiming and determine an eye axis center position on the eyeball; and
when the switching unit switches to the second mode, the switching unit changing an emitting direction of the second light from the second direction to the first direction to let the second light emitted to the eye axis center position on the eyeball to perform an optical measurement.

12. The optical measuring apparatus operating method of claim 11, wherein the second direction is vertical to the first direction.

13. The optical measuring apparatus operating method of claim 11, wherein when the switching unit switches to the first mode, the switching unit is parallel to the first direction, the switching unit is located in a path of the second light emitting toward the second direction to block the second light and the switching unit is located out of a path of the first light emitting toward the first direction.

14. The optical measuring apparatus operating method of claim 11, wherein when the switching unit switches to the second mode, the switching unit is parallel to a direction between the first direction and the second direction, the switching unit is located in a path of the first light emitting toward the first direction to block the first light and the switching unit is located in a path of the second light emitting toward the second direction to change an emitting direction of the second light from the second direction to the first direction, so that the first light and the second light are emitted toward the eyeball alternately.

15. The optical measuring apparatus operating method of claim 11, wherein when the switching unit switches to the second mode, the switching unit is parallel to a direction between the first direction and the second direction, the switching unit is located in a path of the first light emitting toward the first direction to let the first light pass the switching unit and continuously emitted toward the first direction;
the switching unit is located in a path of the second light emitting toward the second direction to change an emitting direction of the second light from the second direction to the first direction, so that the first light and the second light are emitted toward the eyeball simultaneously.

16. An optical measuring apparatus operating method for operating an optical measuring apparatus to perform optical measurement, the optical measuring apparatus comprising a first light source, a second light source and a switching unit, the second light source being disposed parallel to the first light source, the first light source emitting a first light toward a first direction and the second light source emitting a second light toward the first direction, the switching unit selectively switching to a first mode or a second mode, the optical measuring apparatus operating method comprising steps of:
when the switching unit switches to the first mode, the switching unit moving the first light source to let the first light emitted to an aiming region on an eyeball to perform an optical aiming and determine an eye axis center position on the eyeball; and
when the switching unit switches to the second mode, the switching unit moving the second light source to let the second light emitted to the eye axis center position on the eyeball to perform an optical measurement.

17. The optical measuring apparatus operating method of claim 16, wherein when the switching unit switches to the first mode, the switching unit moves the first light source along a second direction, and the second direction is vertical to the first direction.

18. The optical measuring apparatus operating method of claim 16, wherein when the switching unit switches to the second mode, the switching unit moves the second light source along a second direction, and the second direction is vertical to the first direction.

19. The optical measuring apparatus operating method of claim 16, wherein there is a fixed distance between the first light source and the second light source which are disposed in parallel.

20. The optical measuring apparatus operating method of claim 19, wherein when the switching unit switches to the second mode, a distance that the switching unit moves the second light source is the fixed distance.

* * * * *